(12) United States Patent
Williams (10) Patent No.: US 7,678,822 B2
(45) Date of Patent: *Mar. 16, 2010

(54) INDUCTION OF IMMUNE TOLERANCE

(75) Inventor: John M. Williams, Hopkinton, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/714,692

(22) Filed: Mar. 6, 2007

(65) Prior Publication Data

US 2007/0219264 A1 Sep. 20, 2007

Related U.S. Application Data

(63) Continuation of application No. 10/719,701, filed on Nov. 21, 2003, now Pat. No. 7,217,718.

(60) Provisional application No. 60/428,328, filed on Nov. 21, 2002.

(51) Int. Cl.
*A01N 43/50* (2006.01)
*A61K 31/16* (2006.01)

(52) U.S. Cl. ...................... 514/399; 514/613

(58) Field of Classification Search ................. 514/399, 514/613
See application file for complete search history.

(56) References Cited

U.S. PATENT DOCUMENTS

| | | | |
|---|---|---|---|
| 5,540,931 A | 7/1996 | Hewitt et al. | |
| 5,654,312 A | 8/1997 | Andrulis, Jr. et al. | |
| 5,795,967 A | 8/1998 | Aggarwal et al. | |
| 5,801,193 A | 9/1998 | Ojo-Amaize et al. | |
| 5,958,413 A | 9/1999 | Anagnostopulos et al. | |
| 5,990,103 A | 11/1999 | Schonharting et al. | |
| 6,020,323 A | 2/2000 | Cohen et al. | |
| 6,030,615 A | 2/2000 | Bucala et al. | |
| 6,204,245 B1 | 3/2001 | Siegel et al. | |
| 6,211,160 B1 | 4/2001 | Wilson et al. | |
| 6,235,281 B1 | 5/2001 | Stenzel et al. | |
| 6,270,766 B1 | 8/2001 | Feldman et al. | |
| 6,294,170 B1 | 9/2001 | Boone et al. | |
| 6,299,878 B1 | 10/2001 | Pierpadi et al. | |
| 6,306,820 B1 | 10/2001 | Bendele et al. | |
| 6,331,560 B1 | 12/2001 | Shohami et al. | |
| 6,337,325 B1 | 1/2002 | Schonharting et al. | |
| 6,376,665 B1 | 4/2002 | Duan et al. | |
| 6,407,218 B1 * | 6/2002 | Tamarkin et al. ......... 530/389.1 | |
| 6,420,374 B1 | 7/2002 | Bianco et al. | |
| 6,432,962 B2 | 8/2002 | Horneman | |
| 6,432,968 B1 | 8/2002 | Schonharting et al. | |
| 6,503,184 B1 | 1/2003 | Ni et al. | |
| 6,506,569 B1 | 1/2003 | Ni et al. | |
| 6,509,015 B1 | 1/2003 | Salfeld et al. | |
| 6,969,728 B2 * | 11/2005 | Sneddon et al. ............. 514/400 |
| 2002/0119988 A1 | 8/2002 | Sneddon et al. | |
| 2004/0072728 A1 * | 4/2004 | Fawwaz ........................ 514/2 |
| 2004/0163654 A1 | 8/2004 | Williams | |

FOREIGN PATENT DOCUMENTS

| | | |
|---|---|---|
| EP | 0 401 747 A | 12/1990 |
| WO | WO 94/08619 | 4/1994 |
| WO | WO 95/09652 | 4/1995 |
| WO | WO 98/39026 | 9/1998 |
| WO | WO 01/34649 * | 5/2001 |
| WO | WO 01/87849 | 11/2001 |

OTHER PUBLICATIONS

Kunkel et al. Biotherapy 3: 135-141, 1991.*
Yuan, X., et al., "A Novel CD154 monoclonal antibody in acute and chronic rat vascularized cardiac allograft rejection," *Transplantation* 73(11):1736-1742 (2002).
Turner, D.M., et al., "A Genetic Marker of High TNF-α Production in Heart Transplant Recipients," *Transplantation*, 60(10):1113-1117 (1995).
Couriel, D., et al., "TNF-Alpha Inhibition for the Treatment of Chronic GVHD," Blood, 100(11):847a (2002) Abstract.
Hancock, W.W., et al., "Costimulatory function and expression of CD40 ligand, CD80, and CD86 n vascularized murine cardiac allograft rejection," Proc. Natl. Acad. Sci. USA 93:13967-13972 (1996).
Heidenreich, S., et al., "Monocyte Activation for Enhanced Tumour Necrosis Factor-α and Interleukin 6 Production During Chronic Renal Allograft Rejection," *Transplant Immunology*, 2:35-40 (1994).

\* cited by examiner

*Primary Examiner*—Michael G Hartley
*Assistant Examiner*—Shirley V Gembeh
(74) *Attorney, Agent, or Firm*—Hamilton, Brook, Smith & Reynolds, P.C.

(57) ABSTRACT

Methods of inducing immune tolerance by administering an immunosuppressive agent and a compound represented by Formula (I) are disclosed:

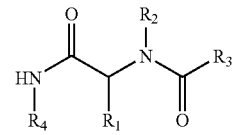

Additionally methods of suppressing an immune response by administering an immunosuppressive agent and a compound represented by Formula (I) are disclosed. Further disclosed are methods for treating autoimmune diseases by administering an immunosuppressive agent and a compound represented by Formula (I). The variables of Formula (I) are described herein.

2 Claims, 2 Drawing Sheets

INDUCTION OF IMMUNE TOLERANCE

RELATED APPLICATIONS

This application is a continuation of U.S. application Ser. No. 10/719,701, filed Nov. 21, 2003 now U.S. Pat. No. 7,217,718, which claims the benefit of U.S. Provisional Application No. 60/428,328, filed Nov. 21, 2002, the entire teachings of which are incorporated herein by reference.

BACKGROUND OF THE INVENTION

Autoimmune disease results when a subject's immune system attacks its own tissues often resulting in severe morbidity or death. Examples of such diseases include type 1 insulin dependent diabetes, multiple sclerosis, rheumatoid arthritis and inflammatory bowel disease.

The immune system also can cause illness as a consequence of its reaction to a transplanted organ, tissue or cell, where the organ, tissue or cell is recognized as foreign. Typically the transplanted organ or tissue is recognized as foreign by the host and infiltrated by the host immune cells, which then carry out their effector function and destroy the transplant. Typical treatments to help suppress the immune response that is elicited by foreign transplant include immunosupressive drugs such as corticosteroids, cyclosporin A, rapamycin and FK506 or antibody therapies such as anti T-cell antibodies. These therapies are not specific and typically must be administered for the life of the patient. Additionally, these therapies have undesirable side effects such as high blood pressure, renal failure, lowered resistance to infection and fever. The costs of those treatments over a lifetime is also quite expensive.

In response to the aforementioned problems associated with immunosupression therapies, there exists a clear need for more efficacious and less problematic therapies to treat autoimmune diseases and organ or tissue rejection.

SUMMARY OF THE INVENTION

It has now been found that compounds of Formula (I), which are described below in detail, and certain immunosupressive agents (e.g., rapamycin or anti CD40L monoclonal antibody) act synergistically to inhibit transplant rejection and can even induce specific immune tolerance towards transplanted tissue. For example, administration of a sub-therapeutic dose of rapamycin together with Compound 1 to mice with heart transplants suppressed transplant rejection for at least 100 days (see Example 1). Rejection did not occur, even after treatment with these drugs was terminated. Furthermore, a second heart transplant from the same donor strain of mice was accepted, while a second heart transplant from an unrelated donor was rejected (Example 3). These results indicate that this combination therapy induced specific immune tolerance towards the transplanted organ without causing non-specific immune ablation. In addition, anti-CD40L monoclonal antibody and Compound 1 were also found to act synergistically to inhibit heart transplant rejection in mice. Mice treated with this combination showed no sign of rejection after 100 days (see Example 2). Based on these results methods of inducing immune tolerance in a subject in which there is an undesired immune response, methods of preventing, inhibiting or suppressing rejection of transplanted organs and methods of treating autoimmune diseases are disclosed herein.

Compound 1

In one embodiment, the present invention provides a method of inducing immune tolerance in a mammal in need of such treatment. The method comprises the step of administering to the mammal an effective amount of an immunosupresive agent and an effective amount of a compound of Formula (I):

(I)

$R_1$ is a substituted or unsubstituted aryl group or a substituted or unsubstituted alkyl group.

$R_2$ is an optionally substituted aralkyl group or an alkyl group substituted with —$NR_5R_6$.

$R_3$ is a substituted or unsubstituted alkyl group or a substituted or unsubstituted aryl group.

$R_4$ a substituted or unsubstituted alkyl group or a substituted or unsubstituted aryl group.

$R_5$ and $R_6$ are independently selected from a substituted or unsubstituted alkyl group or a substituted or unsubstituted aryl group or $R_5$ and $R_6$ taken together with the nitrogen to which they are attached are a non-aromatic heterocyclic group.

In yet another embodiment the present invention provides a method of inhibiting rejection of a transplanted organ, tissue or cell in a mammal. The method comprises the step of administering to the mammal an effective amount of an immunosuppressive agent and an effective amount of a compound of Formula (I).

In yet another embodiment the present invention provides a method for suppressing (or inhibiting) an immune response in a mammal by administering an effective amount of an immunosuppresive agent and an effective amount of a compound of Formula (I).

In another embodiment the present invention is a composition comprising an immunosuppressive agent and a compound of Formula (I). The composition can be used in therapy, for example, to induce specific immune tolerance in a subject in need thereof, to inhibit organ, tissue or cell transplant rejection or to treat autoimmune disease. Typically, the composition comprises an effective amount of both agents. The combination can also be used for the manufacture of a medicament for inducing immune tolerance, treating organ, tissue or cell transplant rejection rejection and/or autoimmune disease.

The immunosupressive drugs used in the combination therapy described herein synergize and therefore are highly effective in suppressing organ transplant rejection. In many instances, the combination induces specific immune tolerance towards the transplanted tissue. As a consequence, treatment can be terminated once tolerance has been induced, thereby eliminating the need to remain on a lifelong regimen of immunosuppressive drugs. In addition, cessation of the immunosuppression allows the immune system to react with full strength against encounters with new antigens. Because the component processes of transplant rejection are shared with a number of autoimmune diseases (e.g., multiple sclerosis, juvenile onset diabetes, inflammatory bowel disease, lupus and rheumatoid arthritis), the disclosed combination therapy is expected to be useful in treating autoimmune disorders as well. Moreover, the disclosed methods can be used to induce tolerance to other types of antigens, including therapeutic agents that would otherwise be recognized as foreign by a subject's immune system, e.g., proteins, protein fragments, viral vectors used for gene therapy and the like.

BRIEF DESCRIPTION OF THE FIGURES

FIG. 1 shows that the Compound 1 synergizes with rapamycin such that cardiac allograft rejection was prevented for all recipients for at least 100 days in this mouse transplant model.

FIG. 2 shows that Compound 1 synergizes with anti-CD 154 monoclonal antibody such that cardiac allograft rejection was prevented in all recipients for at least 100 days in this mouse transplant model.

DETAILED DESCRIPTION OF THE INVENTION

The disclosed invention is a combination therapy of an immunosuppressive drug and the compounds of Formula I.

The combination therapy has been found to synergistically suppress tissue transplant rejection and typically to induce immune tolerance to the transplanted tissue. Tolerance towards other types of antigens, e.g., therapeutic proteins and viral vectors used in gene therapy, can also be induced.

Because the effector mechanisms used by the immune system during tissue transplant rejection are broadly shared with and central to the pathology occurring in a number of autoimmune diseases (e.g., multiple sclerosis, juvenile onset diabetes, inflammatory bowel disease, lupus and rheumatoid arthritis), the combination therapy is also therapeutically useful for treating many immune and/or inflammation based diseases.

The term "immunosuppressive agent" refers to a drug which is able to suppress an immune response and is preferably a drug which suppresses a T cell mediated immune response. Immunosuppressive agents have been commonly used following tissue transplants to suppress acute rejection of the transplanted tissue. Examples of immunosuppressive agents include, but are not limited to, anti-lymphocyte antibodies (e.g., anti-lymphocyte serum, anti-CD3 monoclonal monclonal antibody and anti-CD4 monoclonal antibody), rapamycin, FK506, cyclosporin A, corticosteriods, azathioprine, mycophenolic acid, cytokines, lymphotoxins, inhibitors of costimulatory molecules (e.g., anti CD40L monoclonal antibodies and anti co-stimulatory T-lymphocyte antigen 4 immunoglobulin (CTLA4 Ig)). Rapamycin and inhibitors of co-stimulatory molecules such as anti-CD40L monoclonal antibody are most commonly used in the disclosed combination therapy.

The term "inducing immune tolerance" means rendering the immune system (preferably the T cells of the immune system) unresponsive or less responsive to a particular antigen without inducing a prolonged generalized immune deficiency. The term "antigen" means a substance that is capable of eliciting an immune response. For autoimmune disease, "inducing immune tolerance" means rendering the immune system unresponsive or less responsive towards autoantigen or other antigen that the host recognizes as foreign and against which the host is generating an autoimmune response. Induction of this type of tolerance can be used to treat autoimmune disease. For transplantation, "inducing immune tolerance" means rendering the immune system unresponsive or less responsive towards the antigens on the transplant, the transplanted organ, tissue or cells.

The disclosed methods can be also used to induce immune tolerance towards other types of antigens which evoke an undesired immune response. For example, the safety and efficacy of a wide variety of potential therapeutic agents may be compromised by undesired immune responses to the agent being administered. Inducing tolerance to these agents by the disclosed methods will prevent clearance and destruction of these agents by the immune system and enable them to carry out their therapeutic function. Examples of such agents include therapeutic proteins (e.g., antibodies, enzymes and the like), protein fragments and serums that are obtained from a species different than the host or which otherwise comprise antigen that are recognized as foreign by the host's immune system. Other examples include certain agents used in gene therapy, e.g., viral vectors. "Inducing immune tolerance" to these antigens means rendering the immune system unresponsive or less responsive to the antigen without inducing a prolonged general immune deficiency.

Other types of antigens which evoke undesired immune responses include certain allergens or venoms, particularly when the immune response evoked by these antigens is mediated by T cells. The disclosed methods can be advantageously used to induce tolerance towards antigens of these types. "Inducing immune tolerance" to venoms and allergens means rendering the immune system unresponsive or less responsive to the antigen without inducing a prolonged general immune deficiency.

As described above, the disclosed methods can be advantageously used to treat a mammal with an organ, tissue or cell transplant. The most common type of transplant is an allograft, which is a graft between members of the same species. Cells, tissues or organs (or parts thereof) which are typically transplanted between members of the same species include, but are not limited, to heart, lung, kidney, liver, pancreas, pancreatic islets, brain tissue, cornea, stomach, bone, bone marrow, muscle, intestine, bladder, skin and stem cells. Optionally, the transplanted tissue or organ is bio-engineered, e.g., when the transplanted tissue or organ is grown from a stem cell or other type of precursor cell(s). Bio-engineered tissue or organ can be grown outside of the body and transplanted directly into the host. Alternatively, the precursor cells or immature organ or tissue is transplanted into the host to grow and mature.

The tranplanted organ, tissue or cell(s) can also be a xenograft, i.e., the donor is a member of a species different than the recipient. Xenografts are advantageously used with a bio-engineered tissue or organ, which, instead of being transplanted directly into the recipient in need of the tissue or organ, can be transplanted into a surrogate host such as non-human mammal until a suitable human recipient in need of the bio-engineered tissue or organ is identified. Alternatively, the tissue or organ can be transplanted into the surrogate to allow the bio-engineered tissue or organ to mature. Use of surrogate hosts may be preferred in instances where further development of the tissue or organ is required before transplantation into a human recipient. In another alternative, a xenograft is used when a suitable allograft donor is unavailable. When a transplanting into a different a species, it is desirable to select a host such that the size of the organs in the host and donor are similar. In addition, the host is selected to minimize transmission of communicable diseases.

Autoimmune diseases that may be treated or prevented by the present invention include but are not limited to type 1 insulin dependant diabetes, inflammatory bowel disease, multiple sclerosis, rheumatoid arthritis, dermatitis, rheumatic fever, Graves Disease, Reynauds Syndrome, chronic active hepatitis, atrophic gastritis, Addisons disease, adult respiratory distress syndrome, meningitis, Sjogren's syndrome, Reiter's syndrome, surcoidosis vasculitis, pernicious anemia, Hashimoto's thyroiditis, celiac disease, ankylosing spondylitis, dermatomyositis, pemphigus, pemphigoid, necrotizing vasculitis, myasthenia gravis, lupus erythematosus, leukocyte adhesion deficiency, uveitic encephalitis, polymyositis, granulomatosis, glomerulonephritis, progressive systemic sclerosis, psoriatic arthritis, thrombotic thromibocytopenic purpura, primary binary cirrhosis autoimmune haemolytic anemia, autoimmune complications of AIDS, habitual spontaneous abortions, central nervous system inflammatory disorders, antigen—antibody complex mediated diseases, amyotrophic lateral sclerosis, thyroidosis, scleroderma, lupus, and artherosclerosis. The disclosed combination therapy is expected to be particularly beneficial when used treat type 1 insulin dependant diabetes, inflammatory bowel disease, multiple sclerosis or rheumatoid arthritis.

A "mammal needing treatment to induce immune tolerance" is a mammal with a tissue transplant, a mammal with one of the aforementioned autoimmune diseases or a mammal with an undesired immune response.

An "effective amount" of an immunosuppressive agent and a compound of Formula (I) is an amount which achieves a degree of immunosuppression sufficient to delay, inhibit, suppress or moderate tissue transplant rejection and/or delay, inhibit, suppress or moderate one or more symptoms of an autoimmune disease described herein and/or delay, inhibit, suppress or moderate an undesired immune response to a foreign antigen such as a therapeutic protein, viral vector, allergen, venom and the like. Preferably, the two agents are used at dosages suitable for inducing tolerance to the antigen which is the target of an undesired immune response or, alternatively, at dosages at which the immunosuppressive activities of the two agents synergize. Because many immunosuppresive agents described herein and the compound of Formula (I) act synergistically, sub-therapeutic dosages can be used in the disclosed methods, i.e., dosages which are lower than the amounts that would be effective when the agent is used alone. Suitable sub-therapeutic dosages of one or both agents of the disclosed combination therapy are those which are sufficient, when the two agents are used in combination, to delay, inhibit, suppress or moderate an undesired immune response to an antigen, as described above. The skilled artisan will be able to determine such dosages using ordinary experimentation, such as by using animal models. One advantage of the disclosed combined therapy, therefore, is that the subject being treated can in some instances be spared the side-effects of higher levels of immunosuppression resulting from, for example, corticosteroids and inhibitors of calcineurin.

Suitable dosages of immunosuppressive agents for treating tissue transplant rejection or autoimmune disease are known to one of ordinary skill in the art. Suitable dosages of the compound of Formula (I) are typically those which are described in U.S. patent application Ser. No. 09/852,965 and WO 01/87849 to Sneddon et al., "Modulators of TNF-α Signalling". The entire teachings of these two references are incorporated herein by reference. The dosage to be used is, of course, dependent on various factors such as the mammal to be treated (human or other mammal, weight, sex, age, general health), the severity of the symptoms, the disorder to be treated, possible accompanying disorders if any, the nature of the accompanying treatment with other pharmaceuticals, if any, or the frequency of treatment.

Typically, the combination therapy according to the invention comprises the administration of one to eight individual dosages per day of about 0.01 mg/Kg/day to about 100 mg/Kg/day of the immunosuppressive agent and of about 0.01 mg/Kg/day to about 100 mg/Kg/day of a compound of Formula I. More commonly, about 0.1 mg/Kg/day to about 10 mg/Kg/day of the immunosuppressive agent and of about 0.1 mg/Kg/day to about 10 mg/Kg/day of a compound of Formula (I) are administered and, preferably, about 0.1 mg/Kg/day to about 10 mg/Kg/day of the immunosuppressive agent and of about 0.1 mg/Kg/day to about 1 mg/Kg/day of a compound of Formula (I). The immunosuppressive agents and the compound of Formula (I) can be administered individually or as a mixture of components in a suitably formulated pharmaceutical composition.

The immunosupressive agent and the compound of Formula (I) can be administered prior to exposure to the antigen causing the immune response, while the subject is being exposed to the antigen, following exposure to the antigen or any combination thereof.

The combination preparation according to the invention can also include combination packs or compositions in which the constituents are placed side by side and can therefore be administered simultaneously, separately or sequentially to one and the same human or other mammal body.

A "mammal" is preferably a human, but can also be an animal in need of veterinary treatment, e.g., companion animals (e.g., dogs, cats, rabbits and the like), farm animals (e.g., cows, sheep, pigs, horses, and the like) and laboratory animals (e.g., rats, mice, guinea pigs, and the like).

Pharmaceutically acceptable salts of the compound of Formula (I) can also used in the disclosed combination therapies. The term "pharmaceutically acceptable salts" refers to salts prepared from pharmaceutically acceptable non-toxic acids. Pharmaceutically acceptable salts of compound of Formula (I) can be conveniently prepared from pharmaceutically acceptable non-toxic acids, including inorganic and organic acids, Such acids include for example hydrobromic, hydrochloric, acetic, benzoic, succinic, nitric, sulfuric, benzenesulfuric, camphorsulfonic, ethanesulfonic, citric, fumric, phosphoric, p-toluenesulfonic acid, tantaric, lactic, pamoic, methanesulfonic, maleic, malic, mandelic, gludconic, glutamic, isethionic, mucic, pantothenic and the like.

Pharmaceutical compositions for use in accordance with the present invention thus can be formulated in a conventional manner using one or more physiologically acceptable carriers comprising excipients and auxiliaries which facilitate processing of the active compounds into preparations which can be used pharmaceutically. Proper formulation is dependent upon the route of administration chosen. Techniques for formulation and administration of the components of the instant application can be found Remington: The Science and Practice of Pharmacy. 19$^{th}$ edition, March Publishing Co., Easton Pa. (1995).

Suitable routes of administration can for example include oral, eyedrop, rectal, transmucosal, topical, or intestinal administration; parenternal delivery, including intramuscular, subcutaneous, intramedullary injections as well as intrathecal, direct intraventricular intravenous, intraperitoneal, intranasal, or intraocular injections.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients include fillers such as sugars, (e.g. lactose, sucrose, mannitol, or sorbitol), cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner.

For administration by inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

The compounds can be formulated for parenteral administration by injection, including bolus injection or continuous infusion. Formulations for injection may be presented in unit dosage form, such as in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, such as sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Suitable formulations of this type include biocompatible and biodegradable polymeric hydrogel formulations using crosslinked or water insoluble polysaccharide formulations. Also included are polymerizable polyethylene oxide formulations. Formulations of this type are disclosed in U.S. Pat. Nos. 5,410,016, 4,713,448, 4,636,524, 6,083,524, 5,785,993, 4,937,270 and 5,017,229, the entire teachings of which are incorporated herein by reference. Such long acting formulations may be administered by implantation, for example, subcutaneously or intramuscularly or by intramuscular injection. Preferably, they are implanted in the microenvironment of the transplanted organ or tissue. Thus, for example, the compounds may be formulated with suitable polymeric or hydrophobic materials, for example, as an emulsion in an acceptable oil, or ion exchange resins, or as sparingly soluble derivatives, for example, as a sparingly soluble salt.

The pharmaceutical compositions can also include suitable solid or gel phase carriers or excipients. Examples of such carriers or excipients include calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in an effective amount to achieve the intended purpose. More specifically, an effective amount, as previously defined, denotes an amount suitable for inducing tolerance or suppressing an immune response effective amounts are described above.

The term "aryl group", (e.g., the aryl groups represented by $R_1$, $R_3$ and $R_4$) used alone or as part of a larger moiety such as "aralkyl" (e.g., the aralkyl group represented by $R_2$), refers to carbocyclic aromatic groups such as phenyl, naphthyl, and anthracyl, and heteroaryl groups such as imidazolyl, isoimidazolyl, thienyl, furanyl, pyridyl, pyrimidyl, pyranyl, pyrazolyl, pyrrolyl, pyrazinyl, thiazolyl, isothiazolyl, oxazolyl, isooxazolyl, 1,2,3-triazolyl, 1,2,4-triazolyl, and tetrazolyl.

The term "aryl group", used alone or as part of a larger moiety such as "aralkyl", also includes fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazolyl, quinoxalinyl, quinazolinyl, benzoisothiazolyl, benzooxazolyl, benzoisooxazolyl, benzimidazolyl, quinolinyl, isoquinolinyl and isoindolyl.

The term "aryl group", used alone or as part of a larger moiety such as "aralkyl", also includes carbocyclic aromatic rings or heteroaryl aromatic rings fused to a cycloalkyl group or an non-aromatic heterocyclic group. Examples include indanyl, tetrahydronaphthyl and fluorenyl.

The term "alkyl group" (e.g., the alkyl groups represented by $R_1$-$R_6$), used alone or as part of a larger moiety such as "aralkyl" (e.g., the aralkyl group represented by $R_2$) or "cycloalkylalkyl", is a straight, branched or cyclic non-aromatic hydrocarbon which is completely saturated. Typically, a straight or branched alkyl group has from 1 to about 10 carbon atoms, preferably from 1 to about 4, and a cyclic aliphatic group has from 3 to about 10 carbon atoms, preferably from 3 to about 8. Examples of suitable straight or branched alkyl group include methyl, ethyl, n-propyl, isopropyl, n-butyl, sec-butyl, tert-butyl, pentyl, hexyl, heptyl or octyl; and examples of suitable cycloalkyl groups include cyclopropyl, cyclobutyl, cyclopentyl, cyclohexyl, cycloheptyl and cyclooctyl. A C1-C10 straight or branched alkyl group or a C3-C8 cyclic alkyl group are also referred to as a "lower alkyl" group.

An "aralkyl group" is an alkyl group substituted with one or more aryl groups. A "substituted aralkyl group" can have one or more substituents on the alkyl part of the aralkyl group and/or on the aryl part of the aralkyl group. Suitable aralkyl group substituents are described below in the section providing examples of aryl group substituents and alkyl group substituents.

A "heteroaralkyl group" is an alkyl group substituted with one or more heteroaryl groups. A "substituted heteroaralkyl group" can have one or more substituents on the alkyl part of the heteroaralkyl group and/or on the heteroaryl part of the heteroaralkyl group. Suitable heteroaralkyl group substituents are described below in the section providing examples of aryl group substituents and alkyl group substituents.

A "cycloalkylalkyl group" is an alkyl group substituted with one or more cycloalkyl groups. A "substituted cycloalkylalkyl group" can have one or more substituents on the alkyl part or cycloalkylalkyl part of the cycloalkylalkyl group. Suitable cycloalkylalkyl group substituents are described below in the section providing examples of alkyl group substituents.

A "heterocycloalkylalkyl group" is an alkyl group substituted with one or more non-aromatic heterocyclic groups. A "substituted heterocycloalkylalkyl group" can have one or more substituents on the alkyl part or non-aromatic heterocyclic part of the heterocycloalkylalkyl group. Suitable heterocycloalkylalkyl group substituents are described below in the section providing examples of alkyl group substituents and non-aromatic heterocyclic group substitutents.

The term "non-aromatic heterocyclic ring" (e.g., non-aromatic heterocyclic groups represented by —$NR_5R_6$) refers to non-aromatic ring systems typically having five to fourteen members, preferably five to ten, in which one or more ring carbons, preferably one to four, are each replaced by a heteroatom such as N, O, or S. Examples of non-aromatic heterocyclic rings include 3-1H-benzimidazol-2-one, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrorolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-pthalimidinyl, benzoxanyl, benzopyrrolidinyl, benzopiperidinyl, benzoxolanyl, benzothiolanyl, and benzothianyl.

Suitable substituents for an alkyl group, for a carbon atom on an aryl group or a non-aromatic heterocyclic group are those which do not substantially interfere with the ability of the compound to inhibit transplant rejection. Examples of suitable substituents for a carbon atom of an aryl, alkyl or a carbon atom of a non-aromatic heterocyclic group include —OH, halogen (—Br, —Cl, —I and —F), R, —$CH_2R$, —$OCH_2R$, —$CH_2OC(O)R$, —OR, —O—COR, —COR, —CN, —$NO_2$, —COOH, —$SO_3H$, —$NH_2$, —NHR, —$N(R)_2$, —COOR, —CHO, —$CONH_2$, —CONHR, —$CON(R)_2$, —NHCOR, —NRCOR, —$NHCONH_2$, —NHCONHR, —$NHCON(R)_2$, —$NRCONH_2$, —NRCONHR, —$NRCON(R)_2$, —C(=NH)—$NH_2$, —C(=NH)—NHR, —C((=NH)—$N(R)_2$, —C(=NR)—$NH_2$, —C(=NR)—NHR, —C(=NR)—$N(R)_2$, —NH—C(=NH)—$NH_2$, —NH—C(=NH)—NHR, —NH—C(=NH)—$N(R)_2$, —NH—C(=NR)—$NH_2$, —NH—C(=NR)—NHR, —NH—C(=NR)—$N(R)_2$, —NRH—C(=NH)—$NH_2$, —NR—C(=NH)—NHR, —NR—C(=NH)—$N(R)_2$, —NR—C(=NR)—$NH_2$, —NR—C(=NR)—NHR, —NR—C(=NR)—$N(R)_2$, —$SO_2NH_2$, —$SO_2NHR$, —$SO_2NR_2$, —SH, —$SO_kR$ (k is 0, 1 or 2) and —NH—C(=NH)—$NH_2$. Each R is independently an alkyl, substituted alkyl, benzyl, substituted benzyl, aryl or substituted aryl group. Preferably, R is an alkyl, benzylic or aryl group. In addition, —$N(R)_2$, taken together, can also form a substituted or unsubstituted non-aromatic heterocyclic group, such as pyrollidinyl, piperidinyl, morpholinyl and thiomorpholinyl. Examples of substituents on the alkyl, aryl or benzyl group represented by R include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl. A substituted aryl, alkyl and non-aromatic heterocyclic group can have more than one substitutent.

Suitable substitutents on the nitrogen of a non-aromatic heterocyclic group or heteroaryl group include —R', —N(R')$_2$, —C(O)R', —CO$_2$R', —C(O)C(O)R', —C(O)CH$_2$C(O)R', —SO$_2$R', —SO$_2$N(R')$_2$, —C(=S)N(R')$_2$, —C(=NH)—N(R')$_2$, and —NR'SO$_2$R'; wherein R' is hydrogen, an alkyl group, a substituted alkyl group, phenyl (Ph), substituted Ph, —O(Ph), substituted —O(Ph), CH$_2$(Ph), or an unsubstituted heteroaryl or non-aromatic heterocyclic ring. Examples of substituents on the aliphatic group or the phenyl ring represented by R' include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl.

The synthesis of the compound of Formula (I) can be accomplished using methodologies disclosed in WO 01/87849 and U.S. patent application Ser. No. 09/852,965 previously incorporated by reference in their entirety.

In a preferred embodiment, the variables for the compound represented by Formula (I) are as provided above, provided that the compound is characterized by one or more of the following features:

a) $R_1$ is an optionally substituted aryl group or an optionally substituted $C_1$-$C_4$ aralkyl group.

b) $R_1$ is an optionally substituted phenyl group or an optionally substituted phenyl-$C_1$-$C_4$ alkyl group. Preferred substituents for these values of $R_1$ include $C_1$-$C_4$ alkyl, $C_1$-$C_4$ alkoxy, halogen, CN, $C_1$-$C_4$-alkylthiol, $C_1$-$C_4$-haloalkyl and phenoxy.

c) $R_2$ is an optionally substituted heteroaralkyl group or an alkyl group substituted with —NR$_5$R$_6$.

d) $R_2$ is an optionally substituted imadazolyl-$C_1$-$C_4$-alkyl group or a $C_1$-$C_4$ alkyl group substituted with —NR$_5$R$_6$.

e) $R_2$ is an optionally substituted 2-(imidazol-4-yl)ethyl, an optionally substituted 3-(imidazol-4-yl)propyl, an optionally substituted 3-(imidazol-1-yl)propyl, an optionally substituted 2-(morpholin-4-yl)ethyl, an optionally substituted 2-(4-pyrazolyl)ethyl, an optionally substituted 2-N,N-dimethylaminoethyl or an optionally substituted 3-N,N-dimethylaminopropyl. Preferably, $R_2$ 2-(imidazol-4-yl)ethyl.

f) $R_3$ is an optionally substituted aryl group or an optionally substituted $C_1$-$C_4$ aralkyl group.

g) $R_3$ is an optionally substituted an optionally substituted 2-cyclohexylethyl, an optionally substituted 2-cyclopentylethyl, or an optionally substituted $C_3$-$C_8$ secondary or tertiary alkyl group.

h) $R_3$ is an optionally substituted phenyl, an optionally substituted phenyl-$C_1$-$C_4$-alkyl, an optionally substituted diphenyl-$C_1$-$C_4$-alkyl, an optionally substituted pyrazolyl, an optionally substituted pyrazolyl-$C_1$-$C_4$-alkyl, an optionally substituted indolyl, an optionally substituted indolyl-$C_1$-$C_4$-alkyl, thienylphenyl, thienylphenyl-$C_1$-$C_4$-alkyl, furanylphenyl, furanylphenyl-$C_1$-$C_4$-alkyl, an optionally substituted fluorenyl, an optionally substituted fluorenyl-$C_1$-$C_4$-alkyl, an optionally substituted naphthyl, an optionally substituted naphthyl-$C_1$-$C_4$-alkyl, an optionally substituted quinoxalinyl, an optionally substituted quinoxalinyl-$C_1$-$C_4$-alkyl, an optionally substituted quinazolinyl, an optionally substituted quinazolinyl-$C_1$-$C_4$-alkyl, an optionally substituted pyrolyl, an optionally substituted pyrolyl-$C_1$-$C_4$-alkyl, an optionally substituted thienyl, an optionally substituted thienyl-$C_1$-$C_4$-alkyl, an optionally substituted furanyl, an optionally substituted furanyl-$C_1$-$C_4$-alkyl, an optionally substituted pyridyl or an optionally substituted-$C_1$-$C_4$ pyridyl.

i) $R_3$ is represented by Formula (II):

(II)

Ring A is substituted or unsubstituted; $R_7$ is an optionally substituted phenyl, optionally substituted furanyl, optionally substituted thienyl or optionally substituted pyridyl group; n is an integer from 1-4; and X is a bond, CH$_2$, OCH$_2$, CH$_2$OC(O), CO, OC(O), C(O)O, O, S, SO or SO$_2$. Examples of suitable substituents for Ring A and the aryl groups represented by $R_7$ are provided in section above describing suitable aryl group substituents.

j) $R_3$ is represented by Formula (II), wherein Ring A is substituted or unsubstituted; $R_7$ is an optionally substituted phenyl group; n is 1; and X is CO.

k) $R_3$ is represented by Formula (II), Ring A is unsubstituted $R_7$ is an optionally substituted phenyl group; n is 1; and X is CO. More preferably, $R_7$ is a phenyl group.

l) $R_4$ is an optionally substituted aryl group, an optionally substituted cycloalkyl group, an optionally substituted $C_1$-$C_4$ aralkyl group or an optionally substituted $C_1$-$C_4$ cycloalkylalkyl group.

m) $R_4$ is an optionally substituted phenyl group, an optionally substituted phenyl-$C_1$-$C_4$-alkyl group, an optionally substituted diphenyl-$C_1$-$C_4$-alkyl group, an optionally substituted $C_3$-$C_8$-cycloalkyl-$C_1$-$C_4$-alkyl group or an optionally substituted di-($C_3$-$C_8$-cycloalkyl)-$C_1$-$C_4$-alkyl group.

n) $R_4$ is an optionally substituted benzyl, an optionally substituted diphenylmethyl, an optionally substituted 2-phenylethyl, an optionally substituted 1,2-diphenylethyl, an optionally substituted 2,2-diphenylethyl or an optionally substituted 3,3-diphenylpropyl. Preferred substituents for these values of $R_4$ include $C_1$-$C_4$ alkyl, $C_1$-$C_4$ alkoxy, halogen, CN, $C_1$-$C_4$-alkylthiol, $C_1$-$C_4$-haloalkyl and phenoxy.

In another preferred embodiment, the compound of Formula (I) is characterized by one or more of Features a), f) and l), and preferably all of Features a), f) and l).

In another preferred embodiment, the compound of Formula (I) is characterized by one or more of Features b), h) and m), and preferably all of Features b), h) and m). More preferably, the compound of Formula (I) is additionally characterized by Feature d).

In another preferred embodiment, the compound of Formula (I) is characterized by one or more of Features b), d), i) and m), and preferably all of Features b), d), i) and m). Alternatively, Feature m) is replaced by Feature n). In another alternative, Feature m) is replaced by Feature n) and Feature i) is replaced by Feature j).

In another preferred embodiment, the compound of Formula (I) is characterized by one or more of Features b), d), k) and m), and preferably all of Features b), d), k) and m).

In yet another embodiment, the method of the present invention is carried out with the compound of Formula (III) in place of the compound of Formula (I):

$R_{11}$ is —H, a substituted or unsubstituted aryl, a substituted or unsubstituted aralkyl, a substituted or unsubstituted heteroaryl or a substituted or unsubstituted heteroaralkyl;

$R_{12}$ is alkyl substituted with $NR_{15}R_{16}$, a substituted or unsubstituted aryl, a substituted or unsubstituted heteroaralkyl, or a substituted or unsubstituted heterocycloalkylalkyl;

$R_{13}$ is a substituted or unsubstituted alkyl, a substituted or unsubstituted aryl, a substituted or unsubstituted aralkyl, a substituted or unsubstituted cycloalkylalkyl, a substituted or unsubstituted heteroaryl, a substituted or unsubstituted heteroaralkyl, a substituted or unsubstituted benzophenonyl, or a substituted or unsubstituted cycloalkylalkyl; and each $R_{14}$ is independently, —H, a substituted or unsubstituted alkyl, a substituted or unsubstituted aryl, substituted or unsubstituted aralkyl or a substituted or unsubstituted heteroaralkyl;

$R_{15}$ and $R_{16}$ are independently selected from H, a substituted or unsubstituted alkyl, a substituted or unsubstituted cycloalkyl, a substituted or unsubstituted aryl or unsubstituted aralkyl or $R_{15}$ and $R_{16}$ together with the nitrogen to which they are attached are a heterocycloalkyl.

The invention is illustrated by the following examples, which are not intended to be limiting in any way.

EXEMPLIFICATION

Example 1

Synergistic Suppression of Transplant Rejection Using a Combination Therapy of Compound 1 and Rapamycin in a Mouse Model The ability of a combination therapy of rapamycin and Compound 1 to inhibit transplant rejection in a mouse model was tested. Specifically, the heart from C57/BL6 mice was transplanted into Balb/c recipient mice (total MHC mismatch) using standard protocol described in Hancock, W. W., et al. and Yuan et al., *Transplantation* 73:1736, *Proc. Natl. Acad. Sci. USA* 93: 13967 (1996), the entire teachings of which are incorporated herein by reference. Following surgery, the mice were divided into the following treatment groups:

Group I is a control group that was untreated.

Group II was treated with Compound 1 at a dose of 75 mg/kg/day subcutaneously for fourteen days following surgery.

Group III was treated with rapamycin at a dose of 0.3 mg/kg/day intraperitoneally for three days following surgery.

Group IV was treated with Compound 1 at a dose of 75 mg/kg/day intraperitoneally for fourteen days following surgery and with rapamycin at a dose of 0.3 mg/kg/day intraperitoneally for three days following surgery. It is noted that this dose of rapamycin is about ten times lower than is typically used to suppress transplant rejection.

Figure 1:
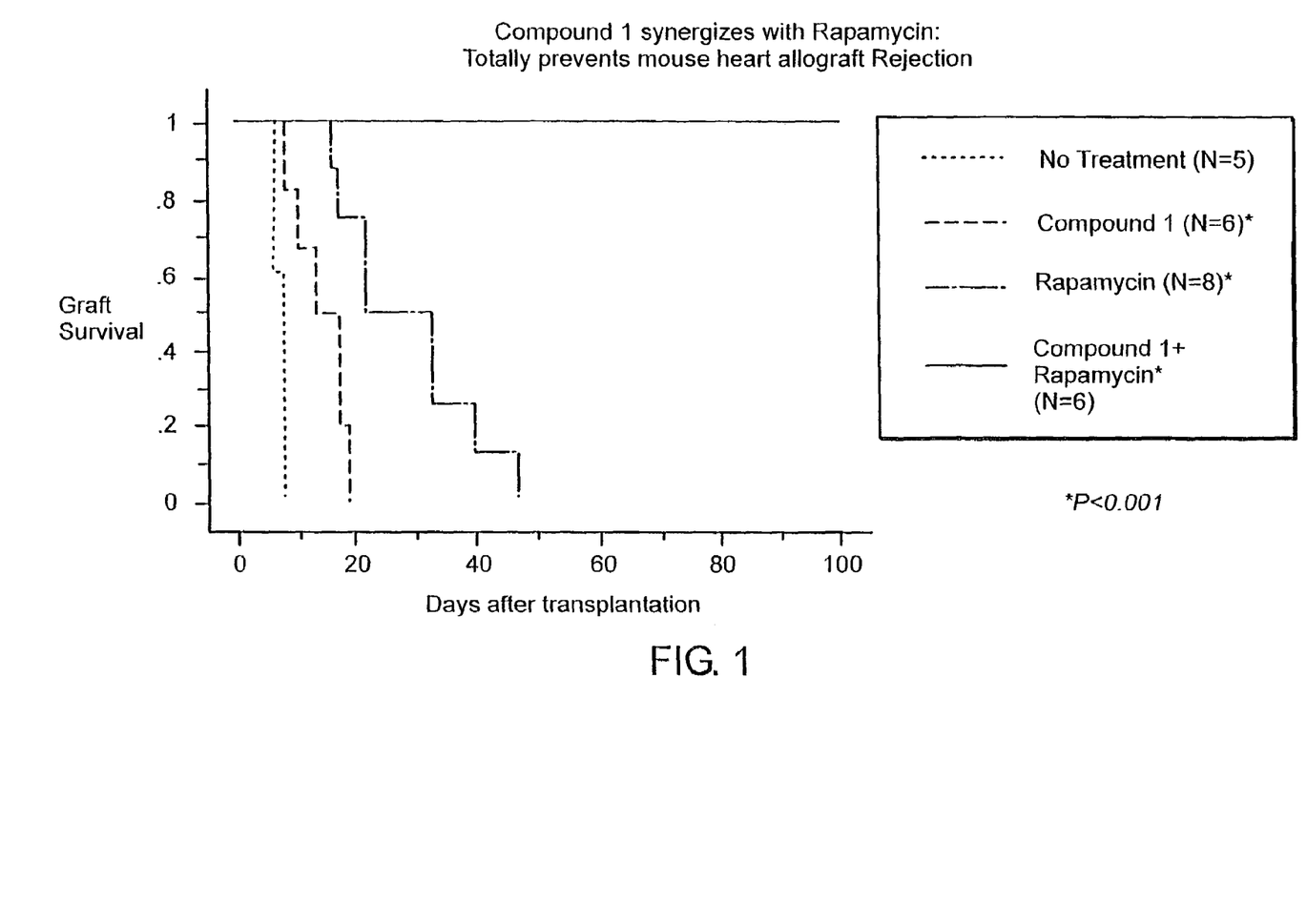
FIG. 1 is a graph showing the survival rate of mice over time (in days) after receiving heart transplant. The mice were divided into four transplanted groups: 1) mice without treatment; 2) mice treated subcutaneously with 0.3 mg/kg/day of rapamycin for three days following the transplant; 3) mice treated intraperitoneally with 75 mg/kg/day of Compound 1 for two weeks following the transplant; and 4) mice treated subcutaneously with 0.3 mg/kg/day of rapamycin for three days and intraperitoneally with 75 mg/kg/day of the compound of Compound 1 for two weeks following the transplant.

The results are shown in FIG. 1. As can be seen, control mice receiving no treatment reproducibly experienced rejection of their transplanted hearts after only ten days. Mice receiving rapamycin alone or the Compound 1 alone showed a modest (two to three weeks) but statistically significant delay ($p<0.001$) in the onset of rejection. However, mice receiving the combination therapy of Compound 1 and rapamycin had 100% graft survival for over 100 days, indicating that the two drugs acted synergistically ($p<0.001$). In fact, the animals treated in this manner never showed signs of acute rejection and were sacrificed at 120 days following surgery so that the transplanted heart could analyzed histologically.

Example 2

Figure 2:
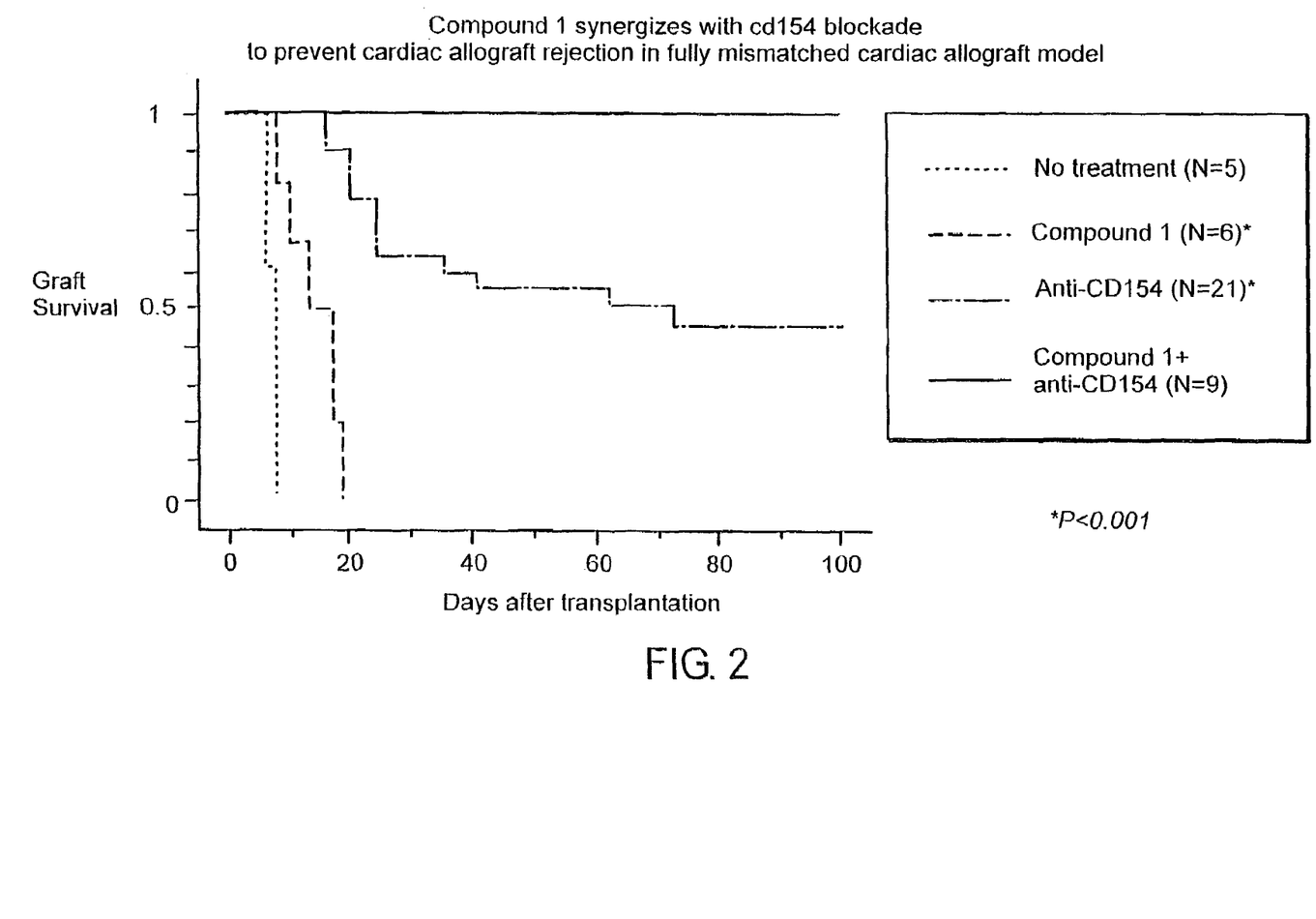
FIG. 2 is a graph showing the survival rate of mice over time (in days) after receiving heart transplant. The mice were divided into four transplanted groups: 1) mice without treatment; 2) mice treated with a single dose of anti-CD 154 monoclonal antibody (250 μg/mouse) immediately following the transplant; 3) mice treated with 75 mg/kg/day of Compound 1 for two weeks following the transplant; and 4) mice treated with a single dose of 250 μg of anti-CD154 monoclonal antibody immediately following transplant and 75 mg/kg/day of Compound 1 for two weeks following the transplant.

Synergistic Suppression of Transplant Rejection Using a Combination Therapy of Compound 1 and Anti-CD40L in a Mouse Model The ability of a combination therapy of anti CD40L and Compound 1 to inhibit transplant rejection in a mouse model was tested according to the protocol of Example 1 using a single 250 μg dose of anti CD40L administered intraperitoneally in place of rapamycin. The results are shown in FIG. 2. As can be seen, mice receiving the combination therapy had 100% graft survival for over 100 days, indicating that the two drugs acted synergistically ($p<0.001$). Again, the animals treated in this manner never showed signs of acute rejection and were sacrificed at 120 days following surgery so that the transplanted heart could analyzed histologically.

Example 3

Induction of Specific Immune Tolerance Using a Combination Therapy of the Compound 1 and Rapamycin in a Mouse Model The ability of a combination therapy of rapamycin and the Compound 1 to induce specific immune tolerance in a mouse model was tested. Specifically, the heart from C57/BL6 mice was transplanted into Balb/c recipient mice (total MHC mismatch) using standard protocol described in Hancock, W. W., et al. *Proc. Natl. Acad. Sci. USA* 93: 13967 (1996) and and Yuan et al., Transplantation 73.1736. Following surgery, the mice were treated with the Compound 1 at a dose of 75 mg/kg/day intraperitoneally for fourteen days and with rapamycin at a dose of 0.3 mg/kg/day intraperitoneally for three days. Following treatment, the mice were divided into two groups of 2 mice each. The first group received a second transplanted heart from the same donor strain of mice; mice from the second group received a second heart transplant from an unrelated third party donor. The hearts from the mice in the first group were not rejected, whereas the all of the mice in second group rejected the new hearts. This indicates that the combination therapy blinds the immune system to the alloantigen immediately at hand for an extended period but does not result in non-specific immune ablation.

Example 4

Effect of a Combination Therapy of the Compound 1 and Cyclosporin A in a Mouse Model The ability of a combination therapy of cyclosporin A and Compound 1 to inhibit transplant rejection in a mouse model was tested according to the protocol of Example 1 using 10 mg/kg/day of cyclosporin A administered intraperitoneally in place of rapamycin. It was observed that the combination of Compound 1 and cyclosporin A appeared not to be synergistic or additive with respect to prolongation of allograft survival.

What is claimed is:

1. A method of inhibiting rejection of a transplanted organ, tissue or cell in a recipient mammal, the method comprising the step of administering to the recipient mammal an effective amount of an anti-lymphocyte antibody and an effective amount of a compound represented by the following structural formula:

or a physiologically acceptable salt of the compound.

2. The method of claim 1 wherein the transplanted organ, tissue or cell is a transplanted heart, kidney, lung, liver, pancreas, skin or bone marrow.

* * * * *